United States Patent
Fujita et al.

(10) Patent No.: US 9,738,520 B2
(45) Date of Patent: Aug. 22, 2017

(54) CHLORINE DIOXIDE GAS GENERATING AGENT PACK, AND MANUFACTURING METHOD AND STORAGE METHOD THEREFOR

(71) Applicant: AMATERA, INC., Aichi (JP)

(72) Inventors: Hiromasa Fujita, Nagoya (JP); Tetsuhiro Fujita, Aichi-gun (JP)

(73) Assignee: AMATERA, INC., Aichi (JP)

( * ) Notice: Subject to any disclaimer, the term of this patent is extended or adjusted under 35 U.S.C. 154(b) by 127 days.

(21) Appl. No.: 14/437,009

(22) PCT Filed: Oct. 24, 2012

(86) PCT No.: PCT/JP2012/077482
§ 371 (c)(1),
(2) Date: Apr. 20, 2015

(87) PCT Pub. No.: WO2014/064782
PCT Pub. Date: May 1, 2014

(65) Prior Publication Data
US 2015/0284249 A1    Oct. 8, 2015

(51) Int. Cl.
*C01B 11/02*    (2006.01)
*A01N 25/18*    (2006.01)
(Continued)

(52) U.S. Cl.
CPC ............ *C01B 11/024* (2013.01); *A01N 25/18* (2013.01); *A61L 2/20* (2013.01); *A61L 9/014* (2013.01);
(Continued)

(58) Field of Classification Search
CPC ...... C01B 11/024; C01B 11/028; A61L 9/014; A61L 9/12; A61L 2/20; A61L 2202/11; A61L 2202/15; A01N 25/18
(Continued)

(56) References Cited

U.S. PATENT DOCUMENTS

| 5,126,070 A | 6/1992 | Leifheit et al. |
| 6,432,322 B1 | 8/2002 | Speronello et al. |

(Continued)

FOREIGN PATENT DOCUMENTS

| CN | 101384507 A | 3/2009 |
| CN | 201553395 U | 8/2010 |

(Continued)

OTHER PUBLICATIONS

International Search Report; PCT/JP2012/077482; Dec. 11, 2012.
(Continued)

*Primary Examiner* — Lessanework Seifu
(74) *Attorney, Agent, or Firm* — Studebaker & Backett PC

(57) ABSTRACT

A chlorine dioxide gas generating agent pack includes a chlorine dioxide gas generating agent containing a mixture of chlorite powder, gas generation control agent powder, moisture-absorbent powder, water-absorbent resin powder, and activating agent powder; and a gas-permeable film container permeable to water vapor and chlorine dioxide gas and containing the chlorine dioxide gas generating agent. This chlorine dioxide gas generating agent pack is suitable for being carried to a region where sterilization, disinfection and deodorization are required.

4 Claims, 2 Drawing Sheets

(51) Int. Cl.
  *A61L 2/20* (2006.01)
  *A61L 9/12* (2006.01)
  *A61L 9/014* (2006.01)

(52) U.S. Cl.
  CPC .............. *A61L 9/12* (2013.01); *C01B 11/028* (2013.01); *A61L 2202/11* (2013.01); *A61L 2202/15* (2013.01)

(58) Field of Classification Search
  USPC .................................................. 422/239, 29
  See application file for complete search history.

(56) References Cited

U.S. PATENT DOCUMENTS

| | | | |
|---|---|---|---|
| 6,699,404 B2 | 3/2004 | Speronello et al. | |
| 7,182,883 B2 | 2/2007 | Speronello et al. | |
| 7,922,984 B2 | 4/2011 | Hamilton et al. | |
| 2009/0078911 A1 | 3/2009 | Shibata et al. | |
| 2012/0012466 A1* | 1/2012 | Sperry ................. | C02F 1/4618 205/334 |

FOREIGN PATENT DOCUMENTS

| | | |
|---|---|---|
| JP | S61-48404 A | 3/1986 |
| JP | H03-70137 U | 7/1991 |
| JP | H03-164403 A | 7/1991 |
| JP | H03-126143 U | 12/1991 |
| JP | H11-116205 A | 4/1999 |
| JP | H11-278808 A | 10/1999 |
| JP | 2000-154003 A | 6/2000 |
| JP | 2001-029442 A | 2/2001 |
| JP | 2002-370910 A | 12/2002 |
| JP | 2005-029430 A | 2/2005 |
| JP | 2005-512769 A | 5/2005 |
| JP | 2005-255657 A | 9/2005 |
| JP | 2006-051485 A | 2/2006 |
| JP | 2006-321666 A | 11/2006 |
| JP | 2007-001807 A | 1/2007 |
| JP | 2007-217239 A | 8/2007 |
| JP | 2009-185043 A | 8/2009 |
| JP | 3171472 U | 10/2011 |
| JP | 2012-177209 A | 9/2012 |

OTHER PUBLICATIONS

An Office Action issued by the Chinese Patent Office on Mar. 2, 2015, which corresponds to Chinese Patent Application No. 201280021407.1.
Information Offer Form issued in Japanese Patent Application No. 2011-116953; Oct. 3, 2013.
Information Offer Form issued in Japanese Patent Application No. 2011-116953; Nov. 5, 2013.
Information Offer Form; issued in Japanese Patent Application No. 2011-116953; Nov. 28, 2014.
An Office Action; "Notice of Grounds of Rejection", issued by the Japanese Patent Office on Jul. 30, 2013, which corresponds to Japanese Patent Application No. 2011-116953.
An Office Action; "Notice of Grounds of Rejection", issued by the Japanese Patent Office on Nov. 12, 2013, which corresponds to Japanese Patent Application No. 2011-116953.
An Office Action; "Notice of Grounds of Rejection", issued by the Japanese Patent Office on Sep. 2, 2014, which corresponds to Japanese Patent Application No. 2011-116953.
Decision to Grant Patent; issued by the Japanese Patent Office on Nov. 25, 2014, which corresponds to Japanese Patent Application No. 2011-116953.

* cited by examiner

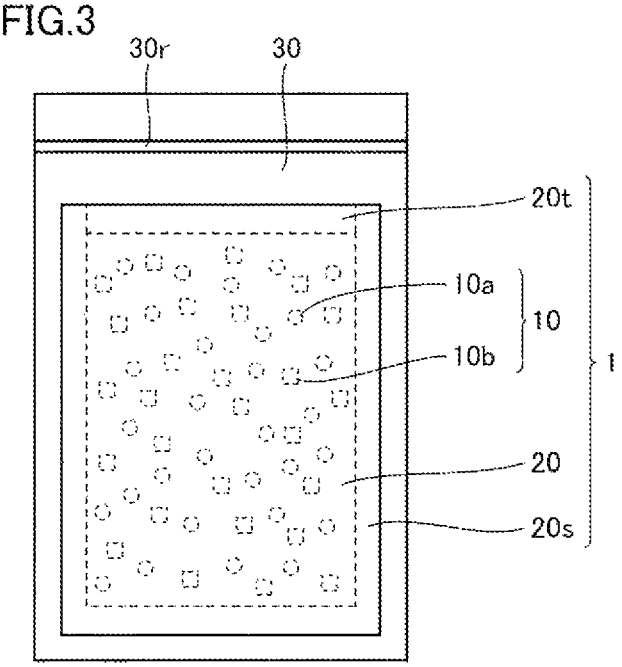

CHLORINE DIOXIDE GAS GENERATING AGENT PACK, AND MANUFACTURING METHOD AND STORAGE METHOD THEREFOR

TECHNICAL FIELD

The present invention relates to a chlorine dioxide gas generating agent pack suitable for being carried, as well as a manufacturing method and a storage method for the chlorine dioxide gas generating agent pack.

BACKGROUND ART

From the standpoint of hygiene improvement in the living environment, ethyl alcohol, sodium hypochlorite aqueous solution, benzalkonium chloride aqueous solution, and the like are used as sterilizers, disinfectants, and/or deodorizers.

These conventional sterilizers, disinfectants, and/or deodorizers, however, may not provide a sufficient sterilization and/or disinfection effect against Noroviruses, influenza viruses, MRSA (methicillin-resistant *Staphylococcus aureus*), and *Pseudomonas aeruginosa*, for example, may not provide a sufficient sterilization or disinfection effect against pathogenic bacteria carried by house dust, pollen and the like, and allergic substances, for example, and may not provide a sufficient deodorizing effect against feces and urine, for example. Moreover, the use of these sterilizers, disinfectants, and/or deodorizers in a high concentration and a large amount leads to problems such as side effects on human bodies and adverse effects due to a residual odor and corrosion after use.

Chlorine dioxide gas, which has potent oxidizing properties, has an extremely high sterilization effect, disinfection effect, and deodorizing effect, compared to the conventional sterilizers, disinfectants, and/or deodorizers mentioned above. Therefore, methods, liquids, and compositions for producing chlorine dioxide gas as a sterilizer, a disinfectant, and/or a deodorizer have been proposed.

Japanese Patent Laying-Open No. 11-278808 (PTD 1), for example, discloses a pure chlorine dioxide liquid having dissolved chlorine dioxide gas, chlorite, and a pH adjuster as components, a gel composition containing a pure chlorine dioxide liquid and a high-water-absorbent resin, a foamable composition containing a pure chlorine dioxide liquid and a foaming agent, a container for containing any of the gel composition and the foamable composition, and so on. Japanese Patent Laying-Open No. 2006-321666 (PTD 2) discloses a method for generating chlorine dioxide gas wherein chlorine dioxide gas is continuously generated from a gel composition obtained by adding, to chlorite aqueous solution, bleaching powder or an isocyanuric acid as an activating agent, a gas generation control agent, and a water-absorbent resin, and by gelling the mixture.

CITATION LIST

Patent Document

PTD 1: Japanese Patent Laying-Open No. 11-278808
PTD 2: Japanese Patent Laying-Open No. 2006-321666

SUMMARY OF INVENTION

Technical Problem

The chlorine dioxide gas generated by the methods disclosed in Japanese Patent Laying-Open No. 11-278808 (PTD 1) and Japanese Patent Laying-Open No. 2006-321666 (PTD 2) described above, by virtue of being a gas, can spread and thereby demonstrate its sterilization effect, disinfection effect, and deodorizing effect over a wide region. These methods, however, have had a problem in that the sterilization effect, disinfection effect, and deodorizing effect diminish as the chlorine dioxide gas travels away from the position where it is generated. Further, in the methods for generating chlorine dioxide gas disclosed in Japanese Patent Laying-Open No. 11-278808 (PTD 1) and Japanese Patent Laying-Open No. 2006-321666 (PTD 2) described above, because dissolved chlorine dioxide gas and/or chlorite are/is reacted with a PH adjuster or an activating agent, a large amount of chlorine dioxide gas is generated at the beginning of the reaction, which makes the gas unsuitable for being carried.

Accordingly, an object of the present invention is to provide a chlorine dioxide gas generating agent pack suitable for being carried to a region where sterilization, disinfection and deodorization are required, as well as a manufacturing method and a storage method for the chlorine dioxide gas generating agent pack.

Solution to Problem

According to one aspect of the invention, there is provided a chlorine dioxide gas generating agent pack including a chlorine dioxide gas generating agent containing a mixture of chlorite powder, gas generation control agent powder, moisture-absorbent powder, water-absorbent resin powder, and activating agent powder; and a gas-permeable film container permeable to water vapor and chlorine dioxide gas, the gas-permeable film container containing the chlorine dioxide gas generating agent.

According to another aspect of the invention, there is provided a method for storing a chlorine dioxide gas generating agent pack, including storing the above-described chlorine dioxide gas generating agent pack in a gas-tight container.

According to still another aspect of the invention, there is provided a method for manufacturing a chlorine dioxide gas generating agent pack including the steps of preparing an agent A by mixing chlorite powder and gas generation control agent powder; preparing an agent B by mixing moisture-absorbent powder, water-absorbent resin powder, and activating agent powder; placing the agent A and the agent B in a gas-permeable film container permeable to water vapor and chlorine dioxide gas; and preparing a chlorine dioxide gas generating agent by mixing the agent A and the agent B in the gas-permeable film container.

The method for manufacturing the chlorine dioxide gas generating agent pack according to the invention may further include, after the step of placing the agent A and the agent B in the gas-permeable film container, the step of placing the gas-permeable film container containing the agent A and the agent B in a gas-tight container, wherein the step of preparing a chlorine dioxide gas generating agent by mixing the agent A and the agent B in the gas-permeable film container may be performed in the gas-tight container.

Advantageous Effects of Invention

According to the present invention, there is provided a chlorine dioxide gas generating agent pack suitable for being carried to a region where sterilization, disinfection and

BRIEF DESCRIPTION OF DRAWINGS

FIG. 3 is a schematic diagram showing an example of a method for storing a chlorine dioxide gas generating agent pack according to the invention.

DESCRIPTION OF EMBODIMENTS

First Embodiment

Figure 1:
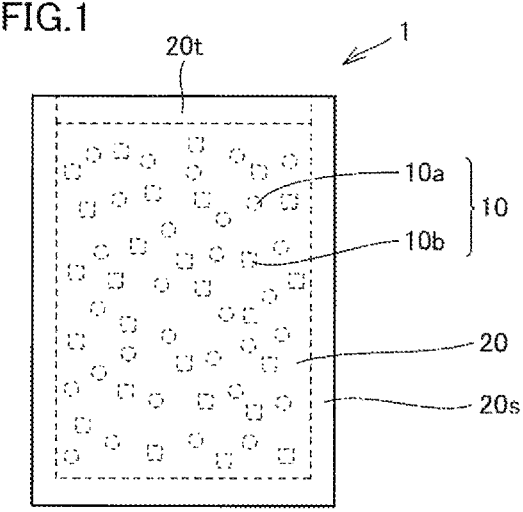
FIG. 1 is a schematic diagram showing an example of a chlorine dioxide gas generating agent pack according to the invention.

With reference to FIG. 1, a chlorine dioxide gas generating agent pack 1 according to one embodiment of the invention includes a chlorine dioxide gas generating agent 10 containing a mixture of chlorite powder, gas generation control agent powder, moisture-absorbent powder, water-absorbent resin powder, and activating agent powder; and a gas-permeable film container 20 permeable to water vapor and chlorine dioxide gas and containing chlorine dioxide gas generating agent 10. In chlorine dioxide gas generating agent pack 1 according to this embodiment, chlorine dioxide gas generating agent 10 is contained (specifically, sealed) in gas-permeable film container 20 permeable to water vapor and chlorine dioxide gas. Thus, when water vapor (humidity) in the air passes through gas-permeable film container 20 to be brought into contact with chlorine dioxide gas generating agent 10, the chlorite powder and the activating agent powder gradually react with each other due to the moisture in the water vapor incorporated into chlorine dioxide gas generating agent 10, so as to gradually produce chlorine dioxide gas. The chlorine dioxide gas produced passes through gas-permeable film container 20 to be released out of chlorine dioxide gas generating agent pack 1.

Chlorine dioxide gas generating agent pack 1 according to this embodiment is suitable for being carried to a region where sterilization, disinfection, and deodorization are required. Further, when chlorine dioxide gas generating agent pack 1 according to this embodiment is tapped several times with the palm or the like, chlorine dioxide gas is generated from chlorine dioxide gas generating agent pack 1. By bringing the palm or the like into contact with the chlorine dioxide gas generated, the palm or the like can be sterilized, disinfected, and deodorized.

{Chlorine Dioxide Gas Generating Agent}

Chlorine dioxide gas generating agent 10 includes a mixture of chlorite powder, gas generation control agent powder, moisture-absorbent powder, water-absorbent resin powder, and activating agent powder. Chlorine dioxide gas generating agent 10, which contains these powders, can incorporate water vapor (humidity) in the air to cause the chlorite powder and the activating agent powder to gradually react with each other, so as to gradually generate chlorine dioxide gas.

(Chlorite Powder)

The chlorite powder is the powder of chlorite. The chlorite powder is not particularly limited as long as it reacts with the activating agent powder in the presence of moisture to produce chlorine dioxide gas. Examples of the chlorite powder include alkali metal chlorite powder such as sodium chlorite ($NaClO_2$) powder, potassium chlorite ($KClO_2$) powder, and lithium chlorite ($LiClO_2$) powder, and alkali earth metal chlorite powders such as calcium chlorite ($Ca(ClO_2)_2$) powder, magnesium chlorite ($Mg(ClO_2)_2$) powder, and barium chlorite ($Ba(ClO_2)_2$) powder. Among the above, sodium chlorite powder, which is designated as a food additive, is highly safe, readily available, and has few restrictions in use. As the sodium chlorite powder, a commercially available 86 mass % product or 79 mass % product, for example, can be suitably used.

(Gas Generation Control Agent Powder)

The gas generation control agent powder refers to powder for causing the chlorine dioxide gas produced by the reaction between the chlorite powder and the activating agent powder in the presence of moisture to be continuously generated from chlorine dioxide gas generating agent 10. Specifically, when the amount of the chlorine dioxide gas produced is large, the gas generation control agent powder holds at least a portion of the chlorine dioxide gas on the surface of and/or inside the powder, and when the amount of the chlorine dioxide gas produced has decreased or no chlorine dioxide gas is produced, it releases the chlorine dioxide gas being held. In this way, the gas generation control agent powder has the function of causing the chlorine dioxide gas to be continuously generated from the chlorine dioxide gas generating agent.

The gas generation control agent is not particularly limited in material and shape as long as it can efficiently distribute the generation of the chlorine dioxide gas. The gas generation control agent, however, is preferably porous with a large surface area, in order to be capable of holding more chlorine dioxide gas. Preferably, the gas generation control agent is at least any selected from the group consisting of sepiolite, montmorillonite, diatomaceous earth, talc, and zeolite. Moreover, in order to provide a large surface area, the gas generation control agent is preferably powdered, granulated, tabular, fibrous, and/or porous.

Among the gas generation control agents mentioned above, sepiolite is preferred because it is excellent at holding and releasing chlorine dioxide gas. As used herein, sepiolite is a natural mineral of a magnesium silicate, whose chemical formula is said to be $Mg_8Si_{12}O_{30}(OH_2)_4(OH)_4 \cdot 8H_2O$. The crystal structure of sepiolite is fibrous and has a number of grooves on its surface, and also has inside a number of clearances having a cylindrical tunnel structure. Sepiolite is therefore a substance with a very large surface area. Note that sepiolite exists in two forms: long fiber-type ($\alpha$) sepiolite that exhibits a clearly fibrous external appearance; and short fiber-type ($\beta$) sepiolite that exhibits a mass- or clay-like external appearance. The short fiber-type sepiolite is preferred in view of safety because it contains no asbestos (a fibrous form of tremolite having a fiber length of 5 μm or more and an aspect ratio of 3 or more). The long fiber-type sepiolite is mainly produced in China, and the short fiber-type sepiolite is mainly produced in Spain, Turkey, and the United States. Sepiolite may be commercially available under the trade name of MIRACLAY® (manufactured by Omi Mining Co., Ltd.), for example.

(Moisture-Absorbent Powder)

The moisture-absorbent powder refers to powder that absorbs the water vapor (humidity) in the air through gas-permeable film container 20, and supplies the moisture to chlorine dioxide gas generating agent 10. The moisture-absorbent powder has the function of causing the chlorine dioxide gas to be produced by the reaction between the chlorite powder and the activating agent powder. Although the moisture-absorbent powder is not particularly limited, calcium chloride ($CaCl_2$) powder, sodium chloride ($NaCl$) powder, magnesium oxide ($MgO$) powder, or the like is preferred because of their high moisture absorbency.

(Water-Absorbent Resin Powder)

The water-absorbent resin powder refers to resin powder that absorbs and holds the moisture supplied to chlorine dioxide gas generating agent 10 by the moisture-absorbent powder to promote the reaction between the chlorite powder and the activating agent powder in chlorine dioxide gas generating agent 10. The water-absorbent resin powder also holds the chlorine dioxide gas produced by the reaction between the chlorite powder and the activating agent powder, and thereby has the function of controlling the generation of chlorine dioxide gas from chlorine dioxide gas generating agent 10, as with the gas generation control agent powder. The water-absorbent resin powder is not particularly limited as long as it absorbs and holds moisture to cause chlorine dioxide gas to be produced from chlorine dioxide gas generating agent 10 and hold the chlorine dioxide gas produced. The water-absorbent resin powder, however, is preferably starch-based water-absorbent resin powder, cellulose-based water-absorbent resin powder, synthetic polymer-based water-absorbent resin powder, or the like, because of their high capacity to hold chlorine dioxide gas. Examples of the starch-based water-absorbent resin powder include starch/polyacrylic acid-based resin (powder, Sanyo Chemical Industries) and the like, and examples of the synthetic polymer-based water-absorbent resin powder include cross-linked polyacrylic acid-based resin powder, isobutylene/maleic acid-based resin powder, Poval/polyacrylate-based resin powder, polyacrylate-based resin powder, and the like. Specifically, sodium polyacrylate powder, for example, is used.

(Activating Agent Powder)

The activating agent powder refers to powder that reacts with chlorite to produce chlorine dioxide gas. The activating agent powder is not particularly limited, and inorganic acid powder, organic acid powder, bleaching powder, isocyanuric acid-based powder, or the like may be used.

The inorganic acid powder is not particularly limited, and may be hydrogen salt powder, which is the powder of a salt obtained by replacing $H^+$ of a polyvalent acid with cations, wherein $H^+$ still remains. Examples thereof include sodium hydrogen sulfate ($NaHSO_4$) powder, potassium hydrogen sulfate ($KHSO_4$) powder, sodium dihydrogen phosphate ($NaH_2PO_4$) powder, disodium hydrogen phosphate ($Na_2HPO_4$) powder, potassium dihydrogen phosphate ($KH_2PO_4$) powder, dipotassium hydrogen phosphate ($K_2HPO_4$) powder, sodium hydrogen carbonate ($NaHCO_3$) powder, and potassium hydrogen carbonate ($KHCO_3$) powder. The hydrogen salt powder for use as the activating agent powder is preferably a hydrogen salt of a strong acid, in order to enhance the production of chlorine dioxide gas. For example, the hydrogen salt powder is preferably any selected from the group consisting of sodium hydrogen sulfate powder, potassium hydrogen sulfate powder, sodium dihydrogen phosphate powder, disodium hydrogen phosphate powder, potassium dihydrogen phosphate powder, and dipotassium hydrogen phosphate powder.

Examples of the organic acid powder include carboxylic acid-based powders such as citric acid powder, malic acid powder, acetic acid powder, formic acid powder, lactic acid powder, tartaric acid powder, and oxalic acid powder. Organic acid powder used as a food additive is preferred because of its high safety.

As the bleaching powder, any of general bleaching powder having an effective chlorine concentration of about 33 mass % to 38 mass % and high test hypochlorite having an effective chlorine concentration of about 60 mass % to 70 mass % may be used. General bleaching powder contains $CaCl_2.Ca(OCl)_2.2H_2O$ as a main component, and contains $Ca(OH)_2$, $CaCl_2$, $Ca(ClO)_2$, $Ca(ClO_3)_2$, and the like as other components. High test hypochlorite contains $Ca(OCl)_2$ as a main component.

Although the isocyanuric acid-based powder (powders of isocyanuric acid and a derivative thereof, as well as a metal salt thereof) is not particularly limited, suitable examples thereof include chlorinated isocyanuric acid powders such as trichloroisocyanuric acid powder and dichloroisocyanuric acid powder, and chlorinated isocyanurate powders such as sodium dichloroisocyanurate powder and potassium dichloroisocyanurate powder, because of their high reactivity with chlorite.

Among these activating agents, organic acid powder used as a food additive is particularly preferred, in order to prepare a safe chlorine dioxide gas generating agent pack capable of being carried with an individual.

Therefore, chlorine dioxide gas generating agent 10 absorbs water vapor (humidity) in the air with the moisture-absorbent powder through gas-permeable film container 20 to incorporate the moisture, and this moisture is absorbed by the water-absorbent resin powder. The chlorite powder and the activating agent powder thus gradually react with each other to gradually produce chlorine dioxide gas. The chlorine dioxide gas produced is held by the water-absorbent resin powder and the gas generation control agent powder. In this way, the chlorine dioxide gas is gradually and continuously generated, and can be continuously released outside through gas-permeable film container 20.

Note that in order to continuously generate chlorine dioxide gas, chlorine dioxide gas generating agent 10 preferably contains 0.01 mass part to 1.0 mass part of the chlorite powder, 0.2 mass part to 5.0 mass parts of the gas generation control agent powder, 0.1 mass part to 2.0 mass parts of the moisture-absorbent powder, 0.25 mass part to 6.0 mass parts of the water-absorbent resin powder, and 0.06 mass part to 1.5 mass parts of the activating agent powder, each calculated as pure form. The proportion of each component, however, is not particularly limited to the above. Moreover, chlorine dioxide gas generating agent 10 preferably contains chlorite in a proportion of 25 mass % or less relative to the total mass of the chlorine dioxide gas generating agent, because the resulting material will not be categorized as a poisonous material. The proportion of the chlorite powder, therefore, is more preferably 0.01 mass part to 0.5 mass part.

{Gas-Permeable Film Container}

Gas-permeable film container 20 refers to a container that sealingly contains chlorine dioxide gas generating agent 10, and is permeable to water vapor and chlorine dioxide gas, but is impermeable to a liquid such as water. Gas-permeable film container 20 is not particularly limited as long as it has high permeability to water vapor and chlorine dioxide gas and low permeability to a liquid such as water. A suitable example of gas-permeable film container 20 may be a container in the form of a bag obtained by sealing outer edges of a gas-permeable film, for example, Typical properties of POWSTO, Type A-1, A-2, A-3, A-4, and A-5 (Japanese Paper Type), as well as Type B-1 and B-2 (Film Type), manufactured by JX Nippon ANCI.

Second Embodiment

Figure 2:
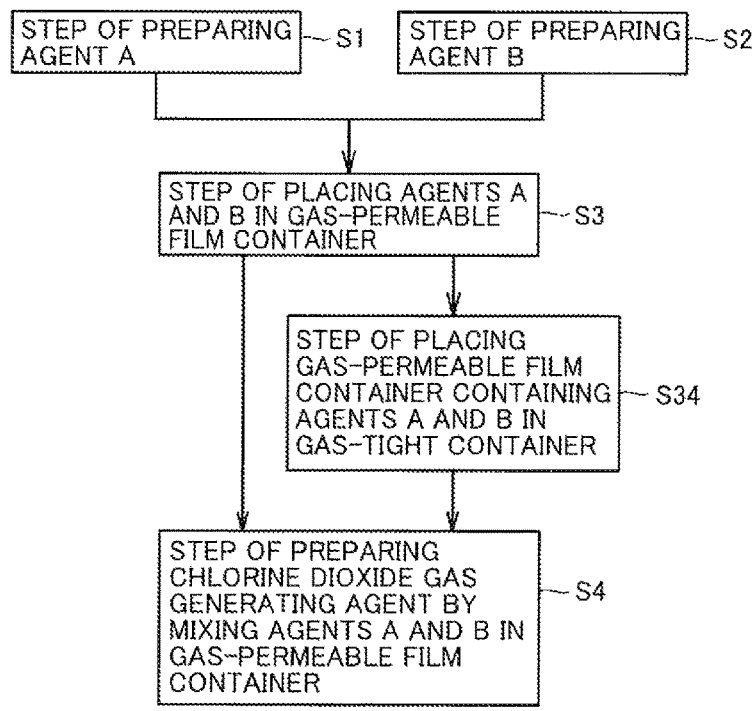
FIG. 2 is a flowchart showing an example of a method for manufacturing a chlorine dioxide gas generating agent pack according to the invention.

With reference to FIGS. 1 and 2, a method for manufacturing a chlorine dioxide gas generating agent pack according to another embodiment of the invention includes step S1 of preparing an agent A 10a by mixing chlorite powder and gas generation control agent; step S2 of preparing an agent B 10b by mixing moisture-absorbent powder, water-absorbent resin powder, and activating agent powder; step S3 of placing agent A 10a and agent B 10b in gas-permeable film container 20 permeable to water vapor and chlorine dioxide gas; and preparing chlorine dioxide gas generating agent 10 by mixing agent A 10a and agent B 10b in gas-permeable film container 20. In the method for manufacturing the chlorine dioxide gas generating agent pack according to this embodiment, agent A 10a containing the chlorite powder and agent B 10b containing the activating agent powder are prepared separately, and then agent A 10a and agent B 10b are mixed in gas-permeable film container 20. In this way, chlorine dioxide gas generating agent pack 1 according to the first embodiment can be efficiently manufactured in high yield.

(S1: Step of Preparing Agent A)

Agent A 10*a* is prepared by mixing the chlorite powder and the gas generation control agent powder. Although the method of mixing the chlorite powder and the gas generation control agent powder is not particularly limited, a mixing method such as shaking, ultrasonic mixing, stirring, high-speed mixing, or the like is suitable, in order to achieve uniform mixing. Note that the chlorite powder and the gas generation control agent powder are as already described in the first embodiment, and thus, the description thereof will not be repeated here.

Agent A 10*a* is preferably mixed in an atmosphere having a relative humidity of 35% or less, using at least any of a dehumidifier and an air-conditioner, in order to prevent or reduce entry of humidity (moisture) in the air. Alternatively, agent A 10*a* may be mixed in a dry air atmosphere or a vacuum atmosphere.

Preferably, the proportion of chlorite in agent A 10*a* is 25 mass % or less relative to the total mass of agent A, because the resulting material will not be categorized as a poisonous material.

(S2: Step of Preparing Agent B)

Agent B 10*b* is prepared by mixing the moisture-absorbent powder, the water-absorbent resin powder, and the activating agent powder. Although the method of mixing the moisture-absorbent powder, the water-absorbent resin powder, and the activating agent powder is not particularly limited, a mixing method such as shaking, ultrasonic mixing, stirring, high-speed mixing, or the like is suitable, in order to achieve uniform mixing. Note that the moisture-absorbent powder, the water-absorbent resin powder, and the activating agent powder are as described in the first embodiment, and thus, the description thereof will not be repeated here.

Agent B 10*b* is preferably mixed in an atmosphere having a relative humidity of 35% or less, using at least any of a dehumidifier and an air-conditioner, in order to prevent or reduce entry of humidity (moisture) in the air. Alternatively, agent B 10*b* may be mixed in a dry air atmosphere or a vacuum atmosphere.

Note that the step of preparing agent A may precede or follow the step of preparing agent B.

(S3: Step of Placing Agent a and Agent B in Gas-Permeable Film Container)

Although the method of placing agent A and agent B in gas-permeable film container 20 is not particularly limited, in order to provide efficient sealing in high yield, it is preferred to place agent A 10*a* and agent B 10*b* in gas-permeable film container 20 through an opening in gas-permeable film container 20 in the form of a bag in which a seal 20*s* is formed on the bottom and opposite sides thereof, and then seal the opening with a seal 20*t*.

In order to prevent or reduce entry of humidity (moisture) in the air into chlorine dioxide gas generating agent 10, it is preferred to place agent A 10*a* and agent B 10*b* in gas-permeable film container 20 and thereafter seal the opening with seal 20*t*, in an atmosphere having a relative humidity of 35% or less, using at least any of a dehumidifier and an air-conditioner. Alternatively, the sealing may be performed in a dry air atmosphere or a vacuum atmosphere.

Although the order of placing agent A 10*a* and agent B 10*b* in gas-permeable film container 20 is not particularly limited, it is preferred to place agent A 10*a* first, and then agent B 10*b*, in order to prevent or reduce entry of moisture into the moisture-absorbent powder and the water-absorbent resin powder.

(S4: Step of Preparing Chlorine Dioxide Gas Generating Agent by Mixing Agent a and Agent B in Gas-Permeable Film Container)

Chlorine dioxide gas generating agent 10 is prepared by mixing agent A 10*a* and agent B 10*b* in gas-permeable film container 20. Although the method of mixing agents A and B is not particularly limited, in order to prevent or reduce entry of humidity (moisture) in the air, and achieve uniform mixing, a preferred mixing method may be as follows, with reference to FIG. 1. Agent A 10*a* and agent B 10*b* are placed into gas-permeable film container 20 having its bottom and opposite sides sealed with seal 20*s*, through the opening in gas-permeable film container 20. Then, after the opening in gas-permeable film container 20 is sealed with seal 20*t*, gas-permeable film container 20 containing agent A 10*a* and agent B 10*b* is shaken from side to side, thereby mixing agent A 10*a* and agent B 10*b* in gas-permeable film container 20.

Moreover, the chlorine dioxide gas generating agent is preferably prepared by mixing agent A 10*a* and agent B 10*b* in an atmosphere having a relative humidity of 35% or less, using at least any of a dehumidifier and an air-conditioner, in order to prevent or reduce entry of humidity (moisture) in the air. Alternatively, the chlorine dioxide gas generating agent may be prepared by mixing agent A 10*a* and agent B 10*b* in a dry air atmosphere or a vacuum atmosphere.

With reference to FIGS. 1 to 3, preferably, the method for manufacturing the chlorine dioxide gas generating agent pack according to this embodiment further includes, after step S3 of placing agent A and agent B in gas-permeable film container 20, step S34 of placing gas-permeable film container 20 containing agent A 10*a* and agent B 10*b* in a gas-tight container 30, wherein the step of preparing chlorine dioxide gas generating agent 10 by mixing agent A 10*a* and agent B 10*b* in gas-permeable film container 20 is performed in gas-tight container 30, in order to prevent or reduce entry of humidity (moisture) in the air into chlorine dioxide gas generating agent 10 during mixing of agents A and B, to thereby prevent or reduce abrupt generation of chlorine dioxide gas.

(S34: Step of Placing Gas-Permeable Film Container Containing Agent a and Agent B in Gas-Tight Container)

With reference to FIG. 3, although the method of placing gas-permeable film container 20 containing agent A 10*a* and agent B 10*b* in gas-tight container 30 is not particularly limited, it is preferred to place gas-permeable film container 20 through an opening in gas-tight container 30, and then seal the opening with a zipper 30*r*, in order to prevent or reduce the entry of humidity (moisture) in the air. Although gas-tight container 30 is not particularly limited, it is preferably a zippered plastic bag, because it is readily sealed repeatedly and provides high workability. Although the material of the zippered plastic bag is not particularly limited as long as it is a material capable of retaining airtightness and impermeable to moisture such as water vapor or water, the zippered plastic bag is preferably made of polyethylene, for example, because it has high airtightness and is readily available.

(S4: Step of Preparing Chlorine Dioxide Gas Generating Agent by Mixing Agent A and Agent B in Gas-Permeable Film Container)

The step of preparing chlorine dioxide gas generating agent 10 by mixing agent A 10*a* and agent B 10*b* in gas-permeable film container 20 after step S34 of placing gas-permeable film container 20 containing agent A 10*a* and agent B 10*b* in gas-tight container 30 is preferably performed in gas-tight container 30. By way of this step, entry of humidity (moisture) into chlorine dioxide gas generating agent 10 can be prevented or reduced during mixing of agents A and B.

Third Embodiment

With reference to FIG. 3, a method for storing a chlorine dioxide gas generating agent pack according to another embodiment of the invention is a method for storing chlorine dioxide gas generating agent pack 1 according to the first embodiment in gas-tight container 30. In the method for storing the chlorine dioxide gas generating agent pack according to this embodiment, chlorine dioxide gas generating agent pack 1 can be stored in gas-tight container 30, and preferably, can be stored in an atmosphere having a relative humidity of 35% or less in gas-tight container 30. This allows the ability to generate chlorine dioxide gas to be maintained for a period of time until use after manufacture of the chlorine dioxide gas generating agent pack, regardless of the length of the period, from a short period of about several hours to a long period of about several years.

In the method for storing the chlorine dioxide gas generating agent pack according to this embodiment, it is preferred to fill the inside of gas-tight container 30 with an atmosphere having a relative humidity of 35% or less. Although the method of filling the inside of gas-tight container 30 with an atmosphere having a relative humidity of 35% or less is not particularly limited, it is preferred, for example, to seal with zipper 30r the opening in gas-tight container 30 containing chlorine dioxide gas generating agent pack 1 in an atmosphere having a relative humidity of 35% or less (for example, in a room having a relative humidity of 35% or less), using a dehumidifier and an air-conditioner. Alternatively, the inside of gas-tight container 30 may be filled with a vacuum atmosphere or a dry air atmosphere.

EXAMPLES

Example 1

1. Preparation of Agent A

In a room adjusted to a temperature of 20° C. and a relative humidity of 30% with an air-conditioner, 8 g of 79 mass % sodium chlorite powder (manufactured by Kanto Chemical Co., Inc.) as the chlorite powder and 20 g of sepiolite (MIRACLAY-P-150 manufactured by Omi Mining Co., Ltd.) as the gas generation control agent powder were placed in a zippered plastic bag (manufactured by Seisan Nipponsha Ltd.) made of polyethylene, having a width of 120 mm and a length of 170 mm, and then the bag was shaken to sufficiently mix the powders in the bag, thereby preparing agent A. Since 6.32 g (8 g×0.79) of sodium chlorite was contained in 28 g of agent A, the sodium chlorite content in agent A was 6.32 g/28 g, namely, 22.6 mass %. Agent A according to this embodiment, therefore, is not categorized as a poisonous material.

2. Preparation of Agent B

Next, in a room adjusted to a temperature of 20° C. and a relative humidity of 30% with an air-conditioner, 10 g of food additive calcium chloride H powder (manufactured by Tomita Pharmaceutical Co., Ltd.) as the moisture-absorbent powder, 22 g of polyacrylate-based water-absorbent resin powder (SANFRESH ST-500G manufactured by Sanyo Chemical Industries) as the water-absorbent resin powder, and 5 g of citric acid powder (manufactured by Fuso Chemical Co., Ltd.) as the activating agent powder were placed in a zippered plastic bag (manufactured by Seisan Nipponsha Ltd.) made of polyethylene, having a width of 120 mm and a length of 170 mm, and the bag was shaken to sufficiently mix the powders in the bag, thereby preparing agent B.

3. Placing of Agents A and B in Gas-Permeable Film Containers

Next, to provide a gas-permeable film container, two sheets having a width of 60 mm and a length of 80 mm of Type A-1 manufactured by JX Nippon ANCI were prepared as gas-permeable films. These sheets were placed over each other with their heat seal surfaces opposing each other, and a heat seal (seal 20s) was formed in a region within 5 mm from the outer edges of the bottom and the opposite sides. Five bag-shaped containers were thus prepared. Next, in a room adjusted to a temperature of 20° C. and a relative humidity of 30% with an air-conditioner, 1 g of agent A and 2 g of agent B were sequentially placed through the opening into each of the containers prepared. Each container was then sealed by forming a heat seal (seal 20t) in the opening of each container containing agents A and B.

4. Preparation of Chlorine Dioxide Gas Generating Agent by Mixing Agents a and B in Gas-Permeable Film Containers Next, the gas-permeable film containers containing agents A and B were placed in a 64 mm-wide and 98 mm-long polyethylene zippered plastic bag (B8 manufactured by Ricchi Corporation) as the gas-tight container, and the plastic bag was airtightly sealed by closing the zipper. The bag was then shaken to mix agents A and B in the gas-permeable film containers. Five chlorine dioxide gas generating agent packs were thus prepared and stored.

5. Measurement of Concentrations of Chlorine Dioxide Gas Generated from Chlorine Dioxide Gas Generating Agent Packs The five chlorine dioxide gas generating agent packs were removed from the gas-tight container, and each chlorine dioxide gas generating agent pack was placed in a paper bag having a width of 70 mm and a length of 110 mm, and allowed to stand in a room. Temperatures and humidities in the room and concentrations of chlorine dioxide gas generated from the chlorine dioxide gas generating agent packs were then measured. In measuring concentrations of chlorine dioxide gas, a gas detection sensor (Toxi RAEII manufactured by RAE Systems) was used for low concentrations from 0 ppm to 1.01 ppm, and a Kitagawa gas detector tube was used for higher concentrations. Concentrations of chlorine dioxide gas were measured by bringing the gas detection sensor into contact with the surface of the paper bag, or by placing a hard vinyl chloride pipe having an inner diameter of 16 mm and a length of 20 mm on the surface of the paper bag containing the chlorine dioxide gas generating agent pack, and then inserting the detector tube into the pipe. The results are summarized in Table 1. In Table 1, a concentration of chlorine dioxide gas is an average value of the five chlorine dioxide gas generating agent packs.

TABLE 1

|  | Time (hr) | | | | | | | | | |
| --- | --- | --- | --- | --- | --- | --- | --- | --- | --- | --- |
|  | 0.5 | 24 | 48 | 72 | 96 | 192 | 240 | 360 | 456 | 744 |
| Temperature (° C.) | 15.0 | 16.0 | 16.0 | 18.0 | 18.0 | 15.0 | 18.0 | 15.0 | 18.0 | 18.0 |
| Humidity (% RH) | 60.0 | 59.0 | 50.0 | 60.0 | 59.0 | 58.0 | 52.0 | 49.0 | 50.0 | 73.0 |
| $ClO_2$ (ppm) | 0.08 | 1.2 | 2.0 | 2.2 | 2.2 | 2.0 | 2.2 | 2.2 | 2.0 | 2.0 |

Example 2

Five chlorine dioxide gas generating agent packs were prepared as in Example 1, except that to form agent A, 4 g of 79 mass % sodium chlorite powder (chlorite powder, manufactured by Kanto Chemical Co., Inc.) and 20 g of sepiolite (gas generation control agent, MIRACLAY-P-150 manufactured by Omi Mining Co., Ltd.) were mixed, and concentrations of chlorine dioxide gas generated from these packs were measured. The results are summarized in Table 2.

TABLE 2

|  | Time (hr) | | | | | | | | | |
|---|---|---|---|---|---|---|---|---|---|---|
|  | 0.5 | 24 | 48 | 72 | 96 | 192 | 240 | 360 | 456 | 744 |
| Temperature (° C.) | 15.0 | 16.0 | 16.0 | 18.0 | 18.0 | 15.0 | 18.0 | 15.0 | 18.0 | 18.0 |
| Humidity (% RH) | 60.0 | 59.0 | 50.0 | 60.0 | 59.0 | 58.0 | 52.0 | 49.0 | 50.0 | 73.0 |
| $ClO_2$ (ppm) | 0.06 | 0.82 | 1.5 | 1.5 | 1.5 | 1.2 | 1.5 | 1.5 | 1.5 | 1.2 |

Example 3

Five chlorine dioxide gas generating agent packs were prepared as in Example 1, except that to form agent A, 2 g of 79 mass % sodium chlorite powder (chlorite powder, manufactured by Kanto Chemical Co., Inc.) and 20 g of sepiolite (gas generation control agent, MIRACLAY-P-150 manufactured by Omi Mining Co., Ltd.) were mixed, and concentrations of chlorine dioxide gas generated from these packs were measured. The results are summarized in Table 3.

TABLE 3

|  | Time (hr) | | | | | | | | | |
|---|---|---|---|---|---|---|---|---|---|---|
|  | 0.5 | 24 | 48 | 72 | 96 | 192 | 240 | 360 | 456 | 744 |
| Temperature (° C.) | 15.0 | 16.0 | 16.0 | 18.0 | 18.0 | 15.0 | 18.0 | 15.0 | 18.0 | 18.0 |
| Humidity (% RH) | 60.0 | 59.0 | 50.0 | 60.0 | 59.0 | 58.0 | 52.0 | 49.0 | 50.0 | 73.0 |
| $ClO_2$ (ppm) | 0.06 | 0.37 | 0.49 | 1.0 | 1.0 | 1.0 | 0.95 | 1.0 | 1.0 | 1.0 |

Example 4

Five chlorine dioxide gas generating agent packs were prepared as in Example 1, except for the following. To provide a gas-permeable film container, two sheets having a width of 60 mm and a length of 80 mm of Type B-2 manufactured by JX Nippon ANCI were prepared as gas-permeable films. These sheets were placed over each other with their heat seal surfaces opposing each other, and a heat seal (seal 20s) was formed in a region within 5 mm from the outer edges of the bottom and the opposite sides. Five bag-shaped containers were thus prepared. Concentrations of chlorine dioxide gas generated from these packs were then measured. The results are summarized in Table 4.

TABLE 4

|  | Time (hr) | | | | | | | | | |
|---|---|---|---|---|---|---|---|---|---|---|
|  | 0.5 | 24 | 48 | 72 | 96 | 192 | 240 | 360 | 456 | 744 |
| Temperature (° C.) | 15.0 | 16.0 | 16.0 | 18.0 | 18.0 | 15.0 | 18.0 | 15.0 | 18.0 | 18.0 |
| Humidity (% RH) | 60.0 | 59.0 | 50.0 | 60.0 | 59.0 | 58.0 | 52.0 | 49.0 | 50.0 | 73.0 |
| $ClO_2$ (ppm) | 0.10 | 1.5 | 2.2 | 2.2 | 2.2 | 2.0 | 2.2 | 2.2 | 2.0 | 2.0 |

Example 5

Five chlorine dioxide gas generating agent packs were prepared as in Example 2, except for the following. To provide a gas-permeable film container, two sheets having a width of 60 mm and a length of 80 mm of Type B-2 manufactured by JX Nippon ANCI were prepared as gas-permeable films. These sheets were placed over each other with their heat seal surfaces opposing each other, and a heat seal (seal 20s) was formed in a region within 5 mm from the outer edges of the bottom and the opposite sides. Five bag-shaped containers were thus prepared. Concentrations of chlorine dioxide gas generated from these packs were then measured. The results are summarized in Table 5.

TABLE 5

| | Time (hr) | | | | | | | | | |
|---|---|---|---|---|---|---|---|---|---|---|
| | 0.5 | 24 | 48 | 72 | 96 | 192 | 240 | 360 | 456 | 744 |
| Temperature (° C.) | 15.0 | 16.0 | 16.0 | 18.0 | 18.0 | 15.0 | 18.0 | 15.0 | 18.0 | 18.0 |
| Humidity (% RH) | 60.0 | 59.0 | 50.0 | 60.0 | 59.0 | 58.0 | 52.0 | 49.0 | 50.0 | 73.0 |
| $ClO_2$ (ppm) | 0.06 | 0.65 | 1.5 | 1.5 | 1.5 | 1.2 | 1.5 | 1.5 | 1.5 | 1.2 |

Example 6

Five chlorine dioxide gas generating agent packs were prepared as in Example 3, except for the following. To provide a gas-permeable film container, two sheets having a width of 60 mm and a length of 80 mm of Type B-2 manufactured by JX Nippon ANCI were prepared as gas-permeable films. These sheets were placed over each other with their heat seal surfaces opposing each other, and a heat seal (seal 20s) was formed in a region within 5 mm from the outer edges of the bottom and the opposite sides. Five bag-shaped containers were thus prepared. Concentrations of chlorine dioxide gas generated from these packs were then measured. The results are summarized in Table 6.

TABLE 6

| | Time (hr) | | | | | | | | | |
|---|---|---|---|---|---|---|---|---|---|---|
| | 0.5 | 24 | 48 | 72 | 96 | 192 | 240 | 360 | 456 | 744 |
| Temperature (° C.) | 15.0 | 16.0 | 16.0 | 18.0 | 18.0 | 15.0 | 18.0 | 15.0 | 18.0 | 18.0 |
| Humidity (% RH) | 60.0 | 59.0 | 50.0 | 60.0 | 59.0 | 58.0 | 52.0 | 49.0 | 50.0 | 73.0 |
| $ClO_2$ (ppm) | 0.06 | 0.47 | 0.92 | 1.2 | 1.2 | 1.0 | 1.2 | 1.0 | 1.0 | 1.0 |

Example 7

Five chlorine dioxide gas generating agent packs were prepared as in Example 1, except for the following. To form agent A, 2 g of 79 mass % sodium chlorite powder (chlorite powder, manufactured by Kanto Chemical Co., Inc.) and 20 g of sepiolite (gas generation control agent, MIRACLAY-P-150 manufactured by Omi Mining Co., Ltd.) were mixed, and to form agent B, 10 g of 72 mass % industrial calcium chloride granular powder (moisture-absorbent powder, manufactured by Central Glass Co., Ltd.), 22 g of polyacrylate-based water-absorbent resin powder (water-absorbent resin powder, SANFRESH ST-500G manufactured by Sanyo Chemical Industries), and 5 g of citric acid powder (activating agent powder, manufactured by Fuso Chemical Co., Ltd.) were mixed. Concentrations of chlorine dioxide gas generated from these packs were then measured. The results are summarized in Table 7.

TABLE 7

| | Time (hr) | | | | | | | | | |
|---|---|---|---|---|---|---|---|---|---|---|
| | 0.5 | 24 | 48 | 72 | 96 | 192 | 240 | 360 | 456 | 744 |
| Temperature (° C.) | 11.0 | 11.0 | 10.0 | 16.0 | 16.0 | 12.0 | 13.0 | 18.0 | 18.0 | 20.0 |
| Humidity (% RH) | 60.0 | 60.0 | 60.0 | 65.0 | 65.0 | 61.0 | 60.0 | 60.0 | 52.0 | 56.0 |
| $ClO_2$ (ppm) | 0.06 | 0.50 | 0.92 | 1.0 | 1.0 | 0.89 | 0.66 | 0.85 | 0.78 | 0.80 |

Example 8

Five chlorine dioxide gas generating agent packs were prepared as in Example 7, except for the following. To form agent A, 2 g of 79 mass % sodium chlorite powder (chlorite powder, manufactured by Kanto Chemical Co., Inc.) and 20 g of synthetic zeolite (gas generation control agent, HSZ-320NAA manufactured by Tosoh Corporation) were mixed. Concentrations of chlorine dioxide gas generated from these packs were then measured. The results are summarized in Table 8.

TABLE 8

| | Time (hr) | | | | | | | | | |
|---|---|---|---|---|---|---|---|---|---|---|
| | 0.5 | 24 | 48 | 72 | 96 | 192 | 240 | 360 | 456 | 744 |
| Temperature (° C.) | 11.0 | 11.0 | 10.0 | 16.0 | 16.0 | 12.0 | 13.0 | 18.0 | 18.0 | 20.0 |
| Humidity (% RH) | 60.0 | 60.0 | 60.0 | 65.0 | 65.0 | 61.0 | 60.0 | 60.0 | 52.0 | 56.0 |
| $ClO_2$ (ppm) | 0.06 | 0.40 | 0.82 | 1.0 | 0.82 | 0.75 | 0.55 | 0.73 | 0.63 | 0.70 |

Example 9

Five chlorine dioxide gas generating agent packs were prepared as in Example 1, except for the following. To form agent A, 2 g of 79 mass % sodium chlorite powder (chlorite powder, manufactured by Kanto Chemical Co., Inc.) and 20 g of sepiolite (gas generation control agent, MIRACLAY-P-150 manufactured by Omi Mining Co., Ltd.) were mixed, and to form agent B, 10 g of special grade reagent calcium chloride powder (moisture-absorbent powder, manufactured by Tomita Pharmaceutical Co., Ltd.), 22 g of polyacrylate-based water-absorbent resin powder (water-absorbent resin powder, SANFRESH ST-500G manufactured by Sanyo Chemical Industries), and 5 g of citric acid powder (activating agent powder, manufactured by Fuso Chemical Co., Ltd.) were mixed. Concentrations of chlorine dioxide gas generated from these packs were then measured. The results are summarized in Table 9.

TABLE 9

| | Time (hr) | | | | | | | | | |
|---|---|---|---|---|---|---|---|---|---|---|
| | 0.5 | 24 | 48 | 72 | 96 | 192 | 240 | 360 | 456 | 744 |
| Temperature (° C.) | 11.0 | 11.0 | 10.0 | 16.0 | 16.0 | 12.0 | 13.0 | 18.0 | 18.0 | 20.0 |
| Humidity (% RH) | 60.0 | 60.0 | 60.0 | 65.0 | 65.0 | 61.0 | 60.0 | 60.0 | 52.0 | 56.0 |
| $ClO_2$ (ppm) | 0.06 | 0.37 | 0.49 | 0.92 | 1.0 | 0.98 | 1.0 | 1.2 | 1.0 | 1.1 |

Example 10

Five chlorine dioxide gas generating agent packs were prepared as in Example 9, except that to form agent A, 4 g of 79 mass % sodium chlorite powder (chlorite powder, manufactured by Kanto Chemical Co., Inc.) and 20 g of sepiolite (gas generation control agent, MIRACLAY-P-150 manufactured by Omi Mining Co., Ltd.) were mixed. Concentrations of chlorine dioxide gas generated from these packs were then measured. The results are summarized in Table 10.

TABLE 10

| | Time (hr) | | | | | | | | | |
|---|---|---|---|---|---|---|---|---|---|---|
| | 0.5 | 24 | 48 | 72 | 96 | 192 | 240 | 360 | 456 | 744 |
| Temperature (° C.) | 11.0 | 11.0 | 10.0 | 16.0 | 16.0 | 12.0 | 13.0 | 18.0 | 18.0 | 20.0 |
| Humidity (% RH) | 60.0 | 60.0 | 60.0 | 65.0 | 65.0 | 61.0 | 60.0 | 60.0 | 52.0 | 56.0 |
| $ClO_2$ (ppm) | 0.06 | 0.47 | 1.0 | 1.2 | 1.5 | 1.5 | 1.5 | 1.5 | 1.5 | 1.5 |

Example 11

Five chlorine dioxide gas generating agent packs were prepared as in Example 10, except that as sepiolite (gas generation control agent), MIRACLAY-P-150 (raw material produced in Turkey, manufactured by Omi Mining Co., Ltd.) was replaced with MIRACLAY-P-200V (raw material produced in the United States, manufactured by Omi Mining Co., Ltd.). Concentrations of chlorine dioxide gas generated from these packs were then measured. The results are summarized in Table 11.

TABLE 11

| | Time (hr) | | | | | | | | | |
|---|---|---|---|---|---|---|---|---|---|---|
| | 0.5 | 24 | 48 | 72 | 96 | 192 | 240 | 360 | 456 | 744 |
| Temperature (° C.) | 11.0 | 11.0 | 10.0 | 16.0 | 16.0 | 12.0 | 13.0 | 18.0 | 18.0 | 20.0 |
| Humidity (% RH) | 60.0 | 60.0 | 60.0 | 65.0 | 65.0 | 61.0 | 60.0 | 60.0 | 52.0 | 56.0 |
| $ClO_2$ (ppm) | 0.06 | 0.47 | 0.95 | 1.0 | 1.2 | 1.5 | 1.5 | 1.5 | 1.5 | 1.5 |

Example 12

Two chlorine dioxide gas generating agent packs were prepared as in Example 9. One of these packs was inserted into a paper bag having a width of 70 mm and a length of 110 mm. The paper bag was then inserted into a pocket of a sweater (from 7:00 to 19:00) or a pocket of pajamas (from 0:00 to 7:00 and from 19:00 to 24:00) that a 63-year-old female subject was wearing. Concentrations of chlorine dioxide gas generated from the pack were then measured. The results are summarized in Table 12. In this example, the paper bag was used to absorb moisture such as sweat, and reduce discomfort due to the chlorine dioxide gas generating agent pack itself. Here, ambient temperatures were measured by a thermometer, and concentrations of chlorine dioxide were measured by bringing a gas detection sensor into contact with the surface of the pocket. During the test, the female subject had no complaints about discomfort due to the chlorine dioxide gas generated.

TABLE 12

| | Time (hr) | | | | | | | | | |
|---|---|---|---|---|---|---|---|---|---|---|
| | 0.5 | 24 | 48 | 72 | 96 | 192 | 240 | 360 | 456 | 744 |
| Temperature (° C.) | 35.1 | 35.2 | 35.2 | 35.2 | 35.2 | 35.2 | 35.2 | 35.2 | 35.2 | 35.3 |
| $ClO_2$ (ppm) | 0.62 | 0.92 | 0.95 | 0.98 | 0.97 | 0.98 | 1.0 | 1.0 | 1.0 | 1.0 |

Further, the other chlorine dioxide gas generating agent pack was inserted into a paper bag having a width of 70 mm and a length of 110 mm. The paper bag was then inserted into a pocket of a dress shirt (from 7:00 to 19:00) or a pocket of pajamas (from 0:00 to 7:00 and from 19:00 to 24:00) that a 70-year-old male subject was wearing. Concentrations of chlorine dioxide gas generated from the pack were then measured as described above. In this example, the paper bag was used to absorb moisture such as sweat, and reduce discomfort due to the chlorine dioxide gas generating agent pack itself. The results are summarized in Table 13. During the test, the male subject had no complaints about discomfort due to the chlorine dioxide gas generated.

TABLE 13

| | Time (hr) | | | | | | | | | |
|---|---|---|---|---|---|---|---|---|---|---|
| | 0.5 | 24 | 48 | 72 | 96 | 192 | 240 | 360 | 456 | 744 |
| Temperature (° C.) | 35.1 | 35.2 | 35.0 | 35.2 | 35.2 | 35.0 | 35.2 | 35.2 | 35.3 | 35.2 |
| $ClO_2$ (ppm) | 0.62 | 0.96 | 0.99 | 0.98 | 0.99 | 0.96 | 0.96 | 1.0 | 0.98 | 1.0 |

As is clear from the foregoing examples, it has been found that the chlorine dioxide gas generating agent pack including a chlorine dioxide gas generating agent containing a mixture of chlorite powder, gas generation control agent powder, moisture-absorbent powder, water-absorbent resin powder, and activating agent powder; and a gas-permeable film container permeable to water vapor and chlorine dioxide gas and sealingly containing the chlorine dioxide gas generating agent, can gradually generate chlorine dioxide gas, and thus, is suitable for being carried to a region where sterilization, disinfection and deodorization are required.

It should be understood that the embodiments and examples disclosed herein are illustrative and non-restrictive in every respect. It is intended that the scope of the present invention is defined by the terms of the claims rather than by the foregoing description, and includes all modifications within the scope and meaning equivalent to the claims.

REFERENCE SIGNS LIST

1: chlorine dioxide gas generating agent pack; 10: chlorine dioxide gas generating agent; 10*a*: agent A; 10*b*: agent B; 20: gas-permeable film container; 20*s*, 20*t*: seal; 30: gas-tight container; 30*r*: zipper

The invention claimed is:

1. A chlorine dioxide gas generating agent pack comprising:
   a chlorine dioxide gas generating agent containing a mixture of an agent A and an agent B, said agent A being a mixture of chlorite powder and gas generation control powder, said agent B being a mixture of moisture-absorbent powder, water-absorbent resin powder, and activating agent powder; and
   a gas-permeable film container permeable to water vapor and chlorine dioxide gas, said gas-permeable film container containing said chlorine dioxide gas generating agent.

2. A method for storing a chlorine dioxide gas generating agent pack, comprising storing the chlorine dioxide gas generating agent pack according to claim 1 in a gas-tight container.

3. A method for manufacturing a chlorine dioxide gas generating agent pack comprising the steps of:
- preparing an agent A by mixing chlorite powder and gas generation control agent powder;
- preparing an agent B by mixing moisture-absorbent powder, water-absorbent resin powder, and activating agent powder;
- placing said agent A and said agent B in a gas-permeable film container permeable to water vapor and chlorine dioxide gas; and
- preparing a chlorine dioxide gas generating agent by mixing said agent A and said agent B in said gas-permeable film container.

4. The method for manufacturing the chlorine dioxide gas generating agent pack according to claim 3, further comprising:
- after the step of placing said agent A and said agent B in said gas-permeable film container, the step of placing said gas-permeable film container containing said agent A and said agent B in a gas-tight container, wherein
- the step of preparing a chlorine dioxide gas generating agent by mixing said agent A and said agent B in said gas-permeable film container is performed in said gas-tight container.

* * * * *